United States Patent
Lenhardt et al.

(10) Patent No.: US 9,478,079 B2
(45) Date of Patent: Oct. 25, 2016

(54) DEVICE FOR MONITORING A SENSOR OF A VEHICLE

(71) Applicant: Robert Bosch GmbH, Stuttgart (DE)

(72) Inventors: Heiko Lenhardt, Limburgerhof (DE); Bernd Kohler, Esslingen (DE); Walter Lehle, Leinfelden (DE); Ipek Sarac, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 9 days.

(21) Appl. No.: 14/567,498

(22) Filed: Dec. 11, 2014

(65) Prior Publication Data

US 2015/0161830 A1    Jun. 11, 2015

(30) Foreign Application Priority Data

Dec. 11, 2013  (DE) .......... 10 2013 225 563

(51) Int. Cl.
| | | |
|---|---|---|
| *G01M 17/00* | (2006.01) | |
| *G07C 5/08* | (2006.01) | |
| *G01K 13/00* | (2006.01) | |
| *G01L 9/00* | (2006.01) | |
| *G01N 27/04* | (2006.01) | |
| *G01W 1/14* | (2006.01) | |
| *G07C 5/00* | (2006.01) | |
| *G01K 15/00* | (2006.01) | |

(52) U.S. Cl.
CPC ............ *G07C 5/0808* (2013.01); *G01K 13/00* (2013.01); *G01K 15/007* (2013.01); *G01L 9/00* (2013.01); *G01N 27/048* (2013.01); *G01W 1/14* (2013.01); *G07C 5/008* (2013.01); *G07C 5/0841* (2013.01)

(58) Field of Classification Search
CPC .. G07C 5/0808; G07C 5/008; G07C 5/0841; G01N 27/048; G01K 13/00; G01W 1/14; G01L 9/00
USPC .................. 701/29.3, 29.5, 30.5, 31.1, 31.4; 340/425.5
See application file for complete search history.

(56) References Cited

U.S. PATENT DOCUMENTS

| | | | | |
|---|---|---|---|---|
| 7,764,188 | B2 * | 7/2010 | O'Neal ..................... | G05B 9/03 340/517 |
| 2006/0229851 | A1 * | 10/2006 | Cannon .................. | G07C 5/008 702/193 |
| 2007/0162550 | A1 * | 7/2007 | Rosenberg ............ | H04L 12/581 709/206 |
| 2008/0189009 | A1 * | 8/2008 | Wang .................. | G01R 31/2829 701/31.1 |
| 2009/0254240 | A1 * | 10/2009 | Olsen, III .............. | G06Q 10/06 701/29.5 |
| 2010/0019891 | A1 * | 1/2010 | Mudalige ............... | G08G 1/163 340/425.5 |
| 2010/0057290 | A1 * | 3/2010 | Brillhart ................ | G06Q 10/06 701/31.4 |
| 2013/0015984 | A1 * | 1/2013 | Yamashiro ............... | G08G 1/22 340/988 |
| 2013/0073139 | A1 * | 3/2013 | Henry ...................... | G07C 5/00 701/29.3 |

FOREIGN PATENT DOCUMENTS

| | | |
|---|---|---|
| DE | 102006007752 | 12/2006 |
| DE | 102006043317 | 3/2008 |

\* cited by examiner

*Primary Examiner* — Shardul Patel

(74) *Attorney, Agent, or Firm* — Norton Rose Fulbright US LLP

(57) ABSTRACT

A method is provided for monitoring at least one sensor of a vehicle, which has means for wireless communication, wherein measured values of the at least one sensor are compared to measured values of at least one comparison vehicle with the aid of the means for wireless communication.

5 Claims, 3 Drawing Sheets

DEVICE FOR MONITORING A SENSOR OF A VEHICLE

BACKGROUND INFORMATION

The legislation on onboard diagnosis for motor vehicles requires that emission-relevant sensors, such as an environmental pressure sensors or temperature sensors be monitored with regard to their functionality. In order to ensure this, a monitoring method is normally used which requires certain stable operating states of the motor vehicle. The offset of a sensor is able to be ascertained, for example, by comparing measured values directly after a cold start of the internal combustion engine, at different times, at different places. If the offset of a sensor is too large, that is, it is outside a tolerance range, one may assume that the sensor is working in a faulty manner.

The disadvantage with known methods is that, depending on the type of sensor to be monitored, redundant sensors have to be present. In a comparison of only 2 present sensors, it cannot be readily determined which of the sensors is operating in a faulty manner. In addition, the abovementioned method cannot be used at all times, since stable operating states of the internal combustion engine have to be present.

SUMMARY

By contrast, the method according to the present invention has the advantage that, using means for wireless communication, measured values of at least one sensor of a vehicle are able to be compared with measured values of at least one comparison vehicle.

Within the scope of the method according to the present invention, however, the comparison of measured values of a plurality of the same or different sensors to the measured values of at least one comparison vehicle is also possible. In the following, by measured values one might designate both the results of individual measurements and the results of series of measurements, or variables derived from it. In this context, the measured values of the at least one comparison vehicle may be measured by identical, similar but also different sensors, as long as the measured values of the comparison vehicle are concerned with the same physical variable as the measured values of the sensor to be monitored. Alternatively, the measured value of the sensor to be monitored may also be compared to measured values of the comparison vehicle, which relate to different physical variables, as long as one is able to convert the measured values of the comparison vehicle to the measured values of the sensor to be monitored, using a clear relationship. The measured values of the comparison vehicle are not limited, however, to measured values measured by sensors. Rather, one should understand by measured values at this point also those values which are formed by model building or by using reference tables.

It is therefore particularly advantageous that the source of the measured values of the comparison vehicle has no part in the ability to carry out the method according to the present invention. A monitoring and/or a calibration of a sensor that is only simply present, are thus possible, independently of the operating state of the internal combustion engine.

It is advantageous if the measured values of the at least one sensor of the vehicle is compared to measured values of at least one comparison vehicle which is located in spatial proximity to the vehicle. It may thus be ensured that the compared measured values represent a physical variable which is submitted to only slight fluctuations. Consequently, estimating the quality of the measured values that are drawn upon for the comparison is also possible. For instance, a measured value of a comparison vehicle may be provided with a quality that is a function of distance. When there is a great distance between the vehicle and the comparison vehicle, the quality of the measured values of the comparison vehicle is lower than at a lower distance between the vehicle and the comparison vehicle.

It is of advantage if the measured values of the at least one sensor of the vehicle are transmitted to an arithmetic unit, the arithmetic unit comparing the measured values of the at least one sensor of the vehicle to the measured values of the at least one comparison vehicle, and ascertaining whether the at least one sensor of the vehicle is operating in a faulty manner. It is also possible that the arithmetic unit, based on the comparison of the measured values of the at least one sensor to the measured values of the at least one comparison vehicle, calibrates the at least one sensor.

It is advantageous if the arithmetic unit compares the measured values of the at least one sensor of the vehicle to measured values of a plurality of comparison vehicles and ascertains by statistical methods whether the at least one sensor of the vehicle is operating in a faulty manner. A greater accuracy of the method may thus be achieved. Within the scope of the method according to the present invention, it is also possible that the at least one sensor of the vehicle is calibrated by the arithmetic unit with the aid of the measured values of the plurality of comparison vehicles.

It is advantageous if the arithmetic unit ascertains that the at least one sensor of the vehicle is operating in a faulty manner when the measured values of the at least one sensor of the vehicle deviates by a specifiable value from the average value of the measured values of the plurality of comparison vehicles. Besides a comparison of the measured values of the at least one sensor of the vehicle to the average value of the measured values of the plurality of comparison vehicles, other comparisons may also be made, such as the comparison to a weighted average. In this instance, the quality of the measured values of the plurality of the comparison vehicles may be drawn upon to form weighting factors for calculating the weighted average. According to one particularly simple exemplary embodiment of the present invention, the weighting factors are formed, in inversely proportional dependence, from the distance between vehicle and comparison vehicle.

It is of advantage if the arithmetic unit is a server outside the vehicle, and the means for wireless communication include an Internet access. Consequently, extensive computing power is available, which also permits the use of numerically lavish statistical analyses. Furthermore, in this way the communication between the vehicle, the comparison vehicles and the arithmetic unit are simplified, since an Internet access represents a standardized interface.

It is also of advantage if the vehicle, when approaching one or more comparison vehicles, communicates directly with the comparison vehicle or the comparison vehicles and receives measured values from the comparison vehicle or the comparison vehicles. Thus, an application of the method according to the present invention is possible even in the non-presence of an external infrastructure for communication, such as to the Internet.

It is advantageous if a flag is set in an electronic storage, in case the measured values of the at least one sensor of the vehicle differ by a specifiable value from the measured values of the comparison vehicle. If only one comparison vehicle is available for the comparison of the measured values, when the measured values deviate, it is at first not possible to decide which of the compared values is faulty. In such a situation, advantageously, the conclusion is not immediately a defective sensor, but it is stored, using a flag, that a deviation between the measured values of the sensor of the vehicle and the measured values of the comparison vehicle has been established. Consequently, faulty diagnoses may be avoided.

If a conclusion is reached of a fault in the at least one sensor of the vehicle, it is advantageous if the measured values of the at least one sensor of the vehicle differ by a specifiable value from the measured values of the comparison vehicle and the fault flag is set in the electronic storage of the vehicle. The fault flag that is set indicates a deviation between the measured values of the at least one sensor of the vehicle and the measured values of a first comparison vehicle at a previous comparison. If this deviation is confirmed at a later comparison between the measured values of the at least one sensor of the vehicle to the measured values of a second comparison vehicle, one may conclude that there is a fault in the at least one sensor of the vehicle.

It is advantageous if the at least one sensor is a humidity sensor or a pressure sensor or a temperature sensor or a brightness sensor or a rain sensor. It is particularly advantageous if the at least one sensor is a sensor which measures the pressure or the temperature or the humidity of the air surrounding the vehicle, since the physical variables characterizing the surrounding air, based on their relative constancy with respect to large spatial scales, are particularly suitable for use within the scope of the method according to the present invention.

A device for monitoring at least one sensor of a vehicle is advantageous, means for wireless communication being present, means for comparing measured values of at least one sensor of the vehicle to measured values of at least one comparison vehicle being present and means being present which ascertain, as a function of the comparison of the measured values of the at least one sensor to the measured values of the at least one comparison vehicle, whether the at least one sensor of the vehicle is operating in a faulty manner. Means for the calibration of the at least one sensor of the vehicle are advantageously present, which calibrate the at least one sensor of the vehicle based on the comparison of the measured values of the at least one sensor of the vehicle to the measured values of the at least one comparison vehicle. Particularly advantageously, in this instance, this is about means for carrying out an offset calibration.

It is also of advantage that for carrying out the method according to the present invention, a computer program is used, which is developed to carry out each step of the method according to the present invention.

This computer program is advantageously stored on an electronic storage medium.

To carry out the method according to the present invention, an electronic control unit is advantageously used, which includes the electronic storage medium.

DETAILED DESCRIPTION

Figure 1:
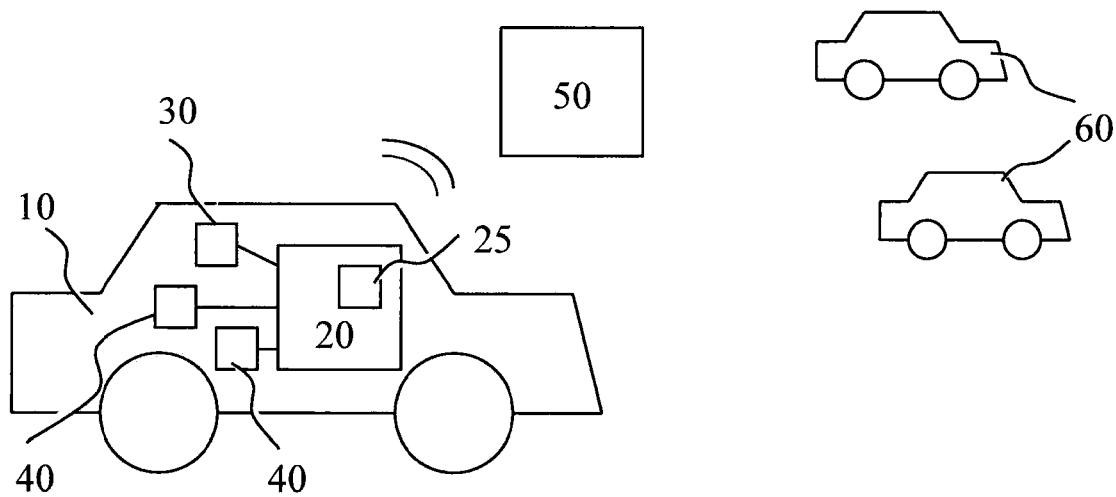
FIG. 1 a schematic representation of a vehicle having a device for carrying out the method according to the present invention according to a first exemplary embodiment.

FIG. 1 shows a vehicle 10 having a device for carrying out the method according to the present invention according to a first exemplary embodiment. Vehicle 10 has an electronic arithmetic unit 20 which is advantageously an electronic control unit, such as an engine control that is present anyhow. The method according to the present invention may also, however, run on other electronic control units, which are either already installed in vehicle 10 for other reasons, or for carrying out the method according to the present invention.

Electronic control unit 20 includes an electronic storage medium 25, on which a computer program is stored that is developed to carry out each step of the method according to the present invention. The electronic storage medium is also used, for example, to store sensor data, results of comparisons, assessments of the state of sensors or characteristic curves of sensors.

Vehicle 10 has at least one sensor 40 which is read out by the electronic arithmetic unit 20. The at least one sensor 40 may particularly be an environmental pressure sensor or an environmental temperature sensor or an air humidity sensor. The method according to the present invention is not limited to the number of sensors 40, so that a plurality of sensors 40 may also be present. In addition, vehicle 10 has means for wireless communication 30. In this context, for example, a UMTS or a WLAN antenna may be involved, which, in a preferred embodiment of the present invention, produces a connection to an external electronic arithmetic unit 50. In one particularly preferred embodiment of the present invention, the external electronic arithmetic unit is an Internet server or a composite of Internet servers.

Comparison vehicles 60, which are located in the vicinity of vehicle 10, also transmit measured values to the external electronic arithmetic unit. The specific number of comparison vehicles 60 not limiting, in this case, for the use of the method according to the present invention. To carry it out, only measured values of at least one comparison vehicle 60 are required. It is unimportant how the measured values of comparison vehicle 60 are obtained, in this context. Then, too, the measured values of comparison vehicles 60 may be measured values which are different from the measured values of the at least one sensor 40. The assumption for carrying out the method according to the present invention is only that a conversion of the measured values of comparison vehicles 60 into measured values which correspond to those of the at least one sensor 40 is possible.

In one advantageous embodiment of the method according to the present invention, external electronic arithmetic unit 50 receives the measured values of the at least one sensor 40 of the vehicle 10, as well as the measured values of comparison vehicles 60. The comparison of the measured values of comparison vehicle 60 to the measured values of the at least one sensor 40 of the vehicle 10 takes place in the external electronic arithmetic unit 50. A calibration of the at least one sensor 40 of the vehicle 10 based on the comparison of the measured value of the at least one sensor 40 to the measured values of comparison vehicle 60 may also take place by the external electronic arithmetic unit 50. The result of the calibration is transmitted, for example, in the form of new characteristic curves or offset values via the means for wireless communication 30 to vehicle 10, and is stored there in electronic storage medium 25 and applied.

In a further preferred specific embodiment of the present invention, the measured values of comparison vehicle 60 are transmitted to vehicle 10 by external electronic arithmetic unit 50. The comparison between the measured values of the at least one sensor 40 of the vehicle and the measured values of comparison vehicle 60 is undertaken, in this case, by electronic arithmetic unit 20 of vehicle 10. The electronic arithmetic unit 20 is preferably an electronic control unit of the vehicle, such as an engine control. A calibration of the at least one sensor 40 of vehicle 10 based on the comparison of the measured value of the at least one sensor 40 to the measured values of comparison vehicle 60 may also take place by the external electronic arithmetic unit 20.

Figure 2:
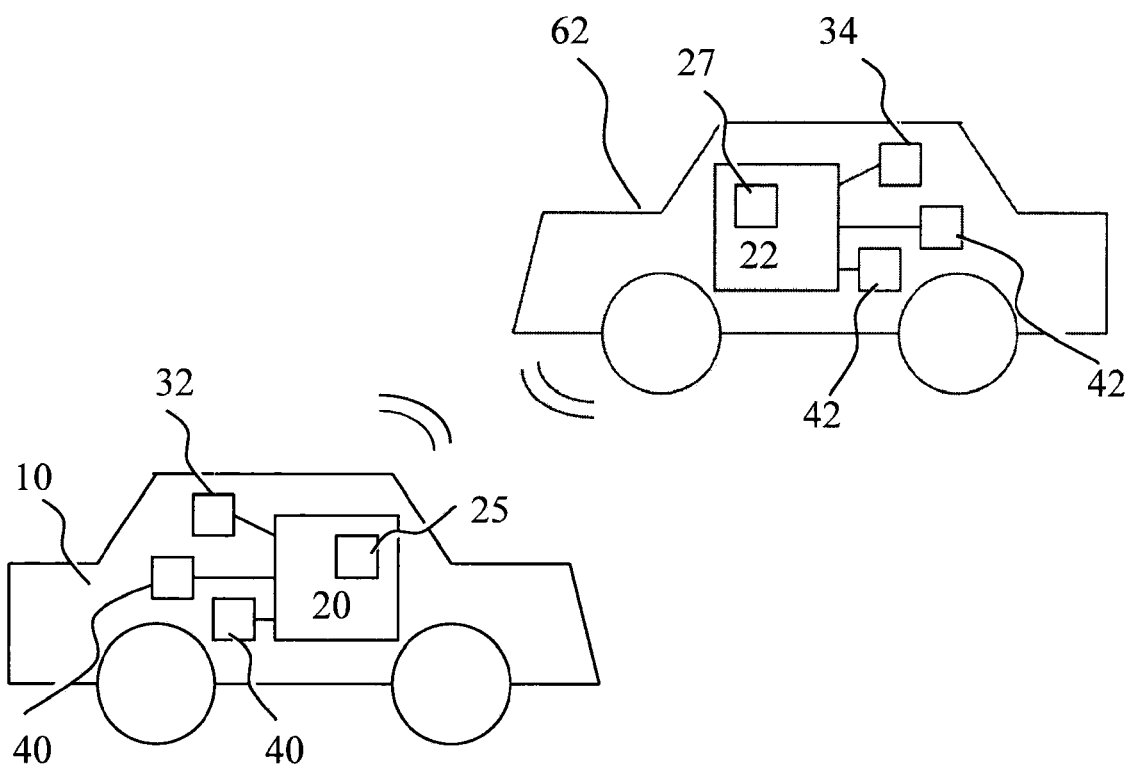
FIG. 2 a schematic representation of a vehicle having a device for carrying out the method according to the present invention according to a second exemplary embodiment.

FIG. 2 shows a schematic representation of a vehicle 10 having a device for carrying out the method according to the present invention according to a second exemplary embodiment. Reference numerals which are also found in FIG. 1 are not described again at this place.

According to a second exemplary embodiment of the present invention, vehicle 10 has means for wireless communication 32, which enable a direct communication with a comparison vehicle 62. The comparison vehicle includes, in this instance, an electronic arithmetic unit 22, an electronic storage medium 27, at least one sensor 42, as well as means for wireless communication 34, which enable a direct communication of comparison vehicle 62 with vehicle 10.

The electronic arithmetic unit 22, the electronic storage medium 27, the at least one sensor 42 and the means for wireless communication 34 of comparison vehicle 62 may be components which are identical to electronic arithmetic unit 20, electronic storage medium 25, the at least one sensor 40 and the means for wireless communication 32 of vehicle 10. However, this is not required for carrying out the method according to the present invention according to the second exemplary embodiment, since it only has to be ensured that the means for wireless communication are compatible.

In the same way, the at least one sensor 40 of vehicle 10 does not have to supply the same measured values as sensors 42 of comparison vehicle 62. Only a clear conversion of the measured values of comparison vehicle 62 into measured values of the at least one sensor 40 of vehicle 10 has to be possible.

Figure 3:
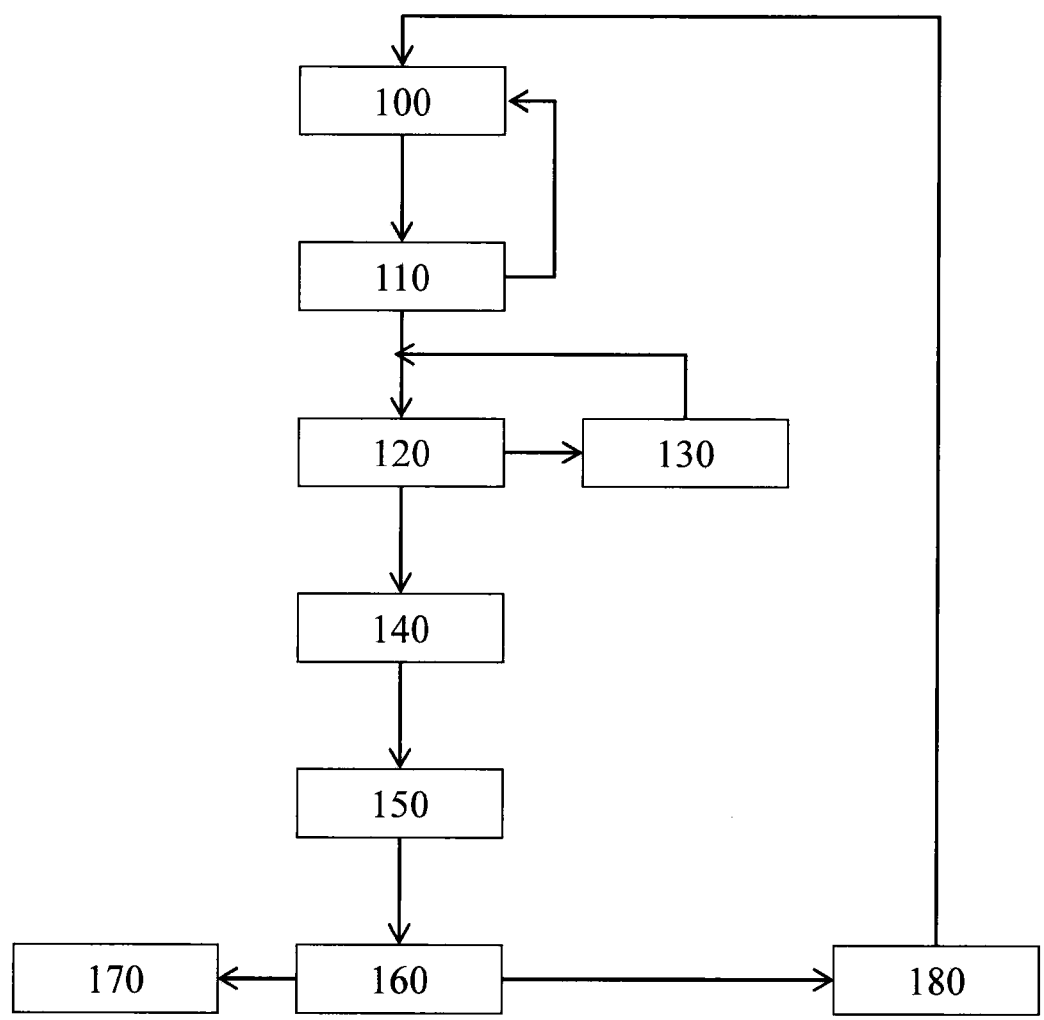
FIG. 3 a schematic representation of the sequence of the method according to the present invention according to the first exemplary embodiment.

FIG. 3 shows a schematic representation of the sequence of the method according to the present invention, according to a first specific embodiment. In step 100 it is checked whether vehicle 10 fulfills initial premises for starting the method. The status of the means for wireless communication 30 may be queried, for example. In step 110 it is tested whether the conditions queried in step 100 are sufficiently satisfied, such as, for instance, whether the means for wireless communication are ready for operation. If this is not the case, step 100 is carried out again. If the premises for carrying out the method according to the present invention exist, the system continues with step 120.

In step 120 it is checked whether a connection to an external electronic arithmetic unit 50 is present. If this is not the case, it is tried in step 130 to make a connection to an external electronic arithmetic unit. If there is a connection, the system continues with step 140.

In alternative embodiments of the method according to the present invention, steps 100, 110, 120 and 130 may be combined and/or regrouped or may be omitted altogether.

In step 140, the measured values of the at least one sensor 40 of the vehicle 10 are transmitted to the external electronic arithmetic unit, where the comparison of the measured values of the at least one sensor 40 of the vehicle 10 to the measured values of the at least one comparison vehicle 60 takes place in step 150 and step 160.

In step 150, a deviation of the measured values of the at least one sensor 40 and the measured values of the at least one comparison vehicle 60 is calculated, in that the difference is formed between the measured values of the at least one sensor 40 from the measured values of the at least one comparison vehicle 60. In one preferred refinement of the method according to the present invention, particularly if a plurality of comparison vehicles is available, for the purpose of calculating the deviation between the measured values of the at least one sensor 40 from the measured values of the comparison vehicle 60, first an average value of the measured values of comparison vehicle 60 is formed. In additional embodiments of the method according to the present invention, a weighted average may be calculated in the average value calculation. In this context, the distance between vehicle 10 and comparison vehicle 60 expediently goes into the calculation of the weighting factor, via an inversely proportional association between distance and weighting factor. It is also possible to use further statistical methods.

In step 160, the deviation between the measured values of the at least one sensor 40 and the measured values of the at least one comparison vehicle 60 is compared to a specifiable value. If the comparison says that the deviation between the measured values of the at least one sensor 40 and the measured values of the at least one comparison vehicle 60 is greater than the specifiable threshold, it is concluded in step 170 that the at least one sensor 40 of vehicle 10 is operating in a faulty manner. In one advantageous refinement of the present invention, it is concluded that there is a fault in the at least one sensor 40 if a deviation between the measured values of the at least one sensor 40 and the measured values of the at least one comparison vehicle 60 repeatedly shows a deviation. For this, a counter may be provided which counts the number of comparisons at which a deviation shows between the measured values of the at least one sensor 40 and the measured values of the at least one comparison vehicle 60.

This information is transmitted via the means for wireless communication 30 to electronic arithmetic unit 20 of the vehicle, where measures may be initiated as a reaction to the sensor detected as operating in a faulty manner. For example, a warning may be output to the driver of vehicle 10, an emergency operation of vehicle 10 may be started and/or, via the means for wireless communication 30, a message may be sent, to a workshop, for example.

If it is determined in step 160 that the deviation between the measured values of the at least one sensor 40 and the measured of the at least one comparison vehicle 60 is less than the specified value, in step 180 the at least one sensor 40 of vehicle 10 is calibrated based on the measured values of the at least one comparison vehicle 60. The result of the calibration is transmitted to the electronic arithmetic unit 20 of the vehicle, for instance, in the form of a characteristic curve. The system subsequently branches to step 100.

In one alternative embodiment of the method according to the present invention, steps 140, 150, 160, 170 and 180 run on an electronic arithmetic unit 20, for instance, the engine controller of vehicle 10. In that case, in step 140, the measured values of the at least one comparison vehicle 60 are received, or an average value of measured values of a plurality of comparison vehicles 60.

Figure 4:
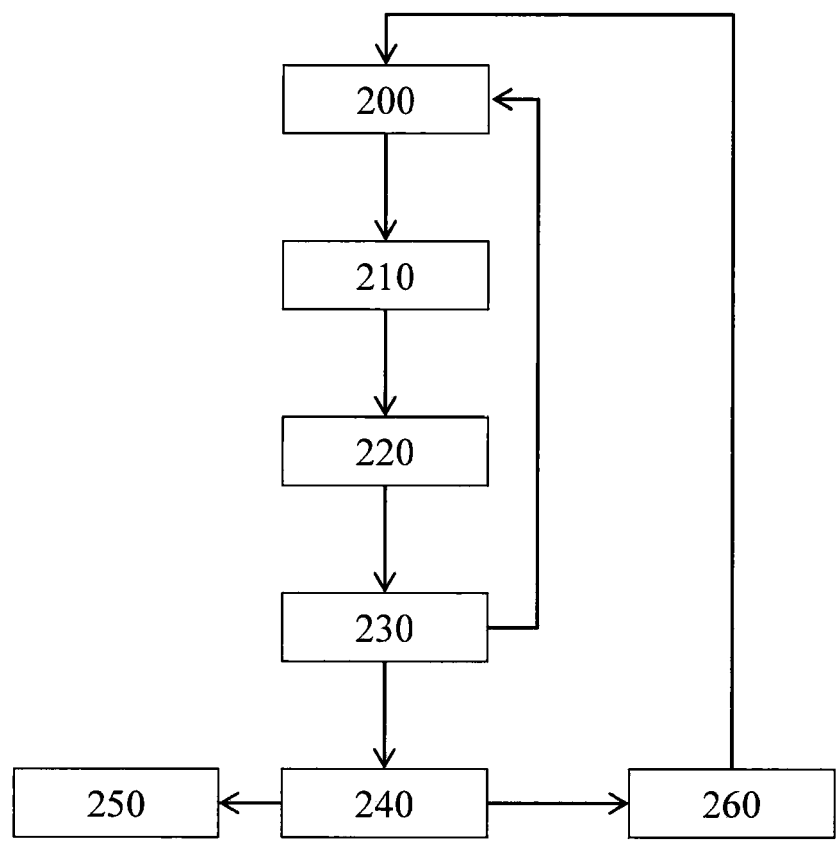
FIG. 4 a schematic representation of the sequence of the method according to the present invention according to the second exemplary embodiment.

FIG. 4 shows a schematic representation of the method according to the present invention, according to the second specific embodiment. It is detected in step 200 that a comparison vehicle 62 is located within the operating range of the means for wireless communication 32 of vehicle 10. The operating range of the means for wireless communication should be selected by using suitable sending/receiving devices in such a way that a comparison vehicle 62 which meets vehicle 10 on a road, is located within the operating range. The communication between vehicle 10 and comparison vehicle 62 takes place directly in this exemplary embodiment, that is, without using an internal infrastructure.

If there is a comparison vehicle 62 within the operating range of the means for wireless communication 32 of vehicle 10, electronic arithmetic unit 20 requests measured values of comparison vehicle 62 and stores these measured values in electronic storage medium 25. The system subsequently continues with step 220.

In step 220, current measured values of the at least one sensor 40 are read in. Subsequently, the measured values of the at least one sensor 40 are compared to the measured values of comparison vehicle 62 in step 230. If this comparison says that the measured values of the at least one sensor 40 differ from the measured values of comparison vehicle 62 by more than a specified value, the system continues with step 240. If the comparison says that the measured values of the at least one sensor 40 deviate from the measured values of the comparison vehicle 62 by less than less than a specified value, a fault flag in electronic storage medium 25 is set to the value "0", and step 200 is carried out again. In one alternative embodiment of the method according to the present invention, a calibration of the at least one sensor 40 of vehicle 10 may also be undertaken in step 230.

In step 240 it is checked whether the fault flag, which is stored in the electronic storage medium 25, has been set to the value "1". If the fault flag is not set, it is set to the value "1" in step 260. Subsequently, step 200 is carried out again. If it is detected in step 240 that the fault flag has already been set to the value "1", it is concluded that sensor 40 of vehicle 10 is operating in a faulty manner.

The use of a fault flag particularly has the advantage that, based on a single deviation between the measured values of the at least one sensor 40 and measured values of comparison vehicle 62, the conclusion of a fault in sensor 40 is not reached directly. Consequently, the use of a fault flag considerably reduces the frequency of false diagnoses.

What is claimed is:

1. A method for monitoring at least one sensor of a vehicle, the vehicle including an arrangement for wireless communication, the method comprising:
   transmitting, with the aid of the arrangement for wireless communication, a measured value of the at least one sensor of the vehicle to an arithmetic unit;
   comparing, by the arithmetic unit, the measured value of the at least one sensor to measured values of sensors of a plurality of comparison vehicles; and
   ascertaining, by the arithmetic unit, whether the at least one sensor is operating in a faulty manner, wherein the arithmetic unit ascertains that the at least one sensor of the vehicle is operating in a faulty manner when the measured values of the at least one sensor of the vehicle deviates by a specifiable value from an average value of the measured values of sensors of the plurality of comparison vehicles.

2. The method as recited in claim 1, wherein:
   the arithmetic unit is a server outside the vehicle.

3. The method as recited in claim 1, wherein the sensor is one of a humidity sensor, a pressure sensor, a temperature sensor, a brightness sensor, and a rain sensor.

4. A device for monitoring at least one sensor of a vehicle, comprising:
   an arithmetic unit; and
   an arrangement for wireless communication, wherein a measured value of the at least one sensor of the vehicle is transmitted to the arithmetic unit;
   wherein the arithmetic unit is configured to:
      compare the measured value of the at least one sensor of the vehicle to measured values of sensors of a plurality of comparison vehicles; and
      ascertain whether the at least one sensor is operating in a faulty manner, wherein the arithmetic unit ascertains that the at least one sensor of the vehicle is operating in a faulty manner when the measured values of the at least one sensor of the vehicle deviates by a specifiable value from an average value of the measured values of sensors of the plurality of comparison vehicles.

5. A non-transitory, computer-readable data storage medium storing a computer program having program codes which, when executed on a computer, perform a method for monitoring at least one sensor of a vehicle, the vehicle including an arrangement for wireless communication, the method comprising:
   transmitting, with the aid of the arrangement for wireless communication, a measured value of the at least one sensor of the vehicle to an arithmetic unit;
   comparing, by the arithmetic unit, the measured value of the at least one sensor to measured values of sensors of a plurality of comparison vehicles; and
   ascertaining, by the arithmetic unit, whether the at least one sensor of the vehicle is operating in a faulty manner, wherein the arithmetic unit ascertains that the at least one sensor of the vehicle is operating in a faulty manner when the measured values of the at least one sensor of the vehicle deviates by a specifiable value from an average value of the measured values of sensors of the plurality of comparison vehicles.

* * * * *